(12) United States Patent
Littig (10) Patent No.: US 7,805,853 B2
(45) Date of Patent: Oct. 5, 2010

(54) TRANSFEMORAL PELVIC IMPRESSION SYSTEM

(76) Inventor: David H Littig, 1645 Donlon St. #102, Ventura, CA (US) 93003

( * ) Notice: Subject to any disclaimer, the term of this patent is extended or adjusted under 35 U.S.C. 154(b) by 1070 days.

(21) Appl. No.: 11/469,364

(22) Filed: Aug. 31, 2006

(65) Prior Publication Data
US 2008/0125776 A1 May 29, 2008

(51) Int. Cl.
*A61B 5/103* (2006.01)
(52) U.S. Cl. .............................. 33/512; 600/587; 606/89
(58) Field of Classification Search ................... 33/512; 600/587; 606/87, 89
See application file for complete search history.

(56) References Cited

U.S. PATENT DOCUMENTS

| | | | | |
|---|---|---|---|---|
| 4,425,713 | A * | 1/1984 | Rotella | 600/587 |
| 4,938,762 | A | 7/1990 | Wehrli | |
| 5,086,779 | A * | 2/1992 | DeLuca et al. | 600/587 |
| 5,141,512 | A * | 8/1992 | Farmer et al. | 606/87 |
| 5,976,145 | A | 11/1999 | Kennefick | |
| 6,002,859 | A | 12/1999 | DiGioia et al. | |
| 6,565,519 | B2 * | 5/2003 | Benesh | 600/587 |
| 6,709,617 | B2 | 3/2004 | Wu | |
| 6,944,518 | B2 | 9/2005 | Roose | |
| 2002/0014017 | A1 * | 2/2002 | Egan | 33/512 |
| 2002/0043738 | A1 | 4/2002 | Wu | |
| 2002/0138022 | A1 * | 9/2002 | Benesh | 600/587 |
| 2004/0107592 | A1 * | 6/2004 | Matlis | 33/512 |
| 2005/0119564 | A1 | 6/2005 | Rosholm et al. | |
| 2005/0245934 | A1 | 11/2005 | Tuke et al. | |
| 2005/0245936 | A1 | 11/2005 | Tuke et al. | |
| 2009/0209963 | A1 * | 8/2009 | Jamali | 606/89 |
| 2009/0222015 | A1 * | 9/2009 | Park et al. | 606/89 |

OTHER PUBLICATIONS

Marlo Ortiz (2004), Handout 1.
Marlo Ortiz (2004), Handout 2.

* cited by examiner

*Primary Examiner*—G. Bradley Bennett
(74) *Attorney, Agent, or Firm*—Sheldon Mak & Anderson (57) ABSTRACT

A system for modeling the pelvic anatomy of a person comprises an apparatus and method for using the apparatus. The apparatus includes a support and a sizing assembly. The support comprises a base and upstanding member. The sizing assembly is movable along the upstanding member to various heights. The sizing assembly includes a pubis stop arm with a pubis stop, and a pelvic seat arm. The pelvic seat arm supports a pair of opposed ischial seats. The pubis arm extends generally horizontally from the upstanding member. The pelvic seat arm has a horizontal ledge for receiving a patient's ischial tuberosity and an adjoining vertical wall for receiving a patient's medial aspect of the ischial ramus. The distance between the pubis stop and pelvic seats is adjustable, the distance between the pelvic seats is adjustable, and the relative angle between the vertical arms of the pelvic seat is adjustable to accommodate for different anatomies.

24 Claims, 8 Drawing Sheets

TRANSFEMORAL PELVIC IMPRESSION SYSTEM

BACKGROUND

Above knee amputees require a correctly constructed effective artificial prosthetic limb to be able to effectively walk. If the socket of the prosthesis is not properly configured lack of patient stability, inability to effectively walk, impingement and/or dislocation can occur. Discussions of prosthetic systems can be found in U.S. Pat. Nos. 4,938,762, 6,002,859, 6,709,617, 6,944,518, Publication Nos. 2002/0043738, 2005/0245934, and 2005/0245936.

Current systems for designing prosthesis are generally unsatisfactory. For example, they concentrate only on the amputated limb, and do not consider the overall effect of the anatomy of the entire pelvic region on the stability of the prosthesis. It is well-known that the pelvic regions of males and females differ significantly, and many systems do not accommodate these differences. Moreover, when fitting the prosthesis, tissue surrounding the bone, and particular muscular tissue, interferes with measuring and fitting the prosthesis.

Accordingly, there is a need for a system for accurately fitting a transfemoral amputee with a prosthesis that accommodates the variations that occur in the pelvic region of patients, and that allows a practitioner to appropriately accommodate for the surrounding tissue.

SUMMARY

The present invention provides a system that satisfies this need, yielding a stable, well-fitted, and comfortable prosthesis for above knee amputees.

The system includes an apparatus for modeling the pelvic anatomy of a person. The apparatus has a sizing assembly movable vertically to selected positions to accommodate persons of different leg length and adjustment means for adjusting the vertical position of the sizing assembly. The adjustment means can comprise an upstanding member that supports the sizing assembly where the sizing assembly is movable along the upstanding member. There can be a base supporting the upstanding member.

The sizing assembly comprises a pubis stop arm having a pubis stop thereon and a pelvic seat arm. The pelvic seat arm supports a pair of opposed ischial seats. The pelvic seat arm extends generally horizontally from the upstanding member and is below the pubis stop. Each ischial seat has a horizontal ledge for receiving a person's ischial tuberosity and an adjoining vertical wall for receiving a person's medial aspect of the ischial ramus. To accommodate different pelvic anatomies, the distance between the pubis stop and the ischial seats is adjustable, the distance between the ischial seats is adjustable, and the relative angle between the vertical walls of the ischial seat is adjustable. Thus the apparatus comprises means for adjusting the distance between the pubis stop and the ischial seats, means for adjusting the distance between the ischial seats, and means for adjusting the relative angle between the vertical walls of the ischial seat.

Preferably the apparatus has at least one handle so that a person missing a portion of a leg can support themselves. Preferably the upstanding member supports the handle.

Preferably the pelvic seat arm can pivot downwardly to be out of the way.

The pubis stop arm extends generally horizontally from the upstanding member and its length can be adjustable such as being made of two telescoping members, thus providing the means for adjusting the distance between the pubis stop and the ischial seats.

The means for adjusting the relative angle between the vertical walls of the ischial seat can be linkages mounted to pivot.

The system includes a method for fitting a patient for an above knee prosthetic. In the method, the vertical position of the sizing assembly and the length of the pubis stop arm are adjusted to position the pubis stop against the patient pubis, and the pelvic seat is positioned against the patient's ischial tuberosity and medial aspect of the ischial ramus. The pelvic seat can then be pivoted downwardly, and the patient's residual leg end is wrapped with a plaster bandage. The pelvic seat is then pivoted back into position to apply pressure to both the pubis stop and pelvic seat to ensure a proper impression.

Optionally, a thin plastic cover is placed on the ischial seat when the person is initially positioned to accommodate for the thickness of the plaster bandage. The cover is removed before the pelvic seat is rotated back into contact with the patient.

The system provides a plaster cast that can be used to mold a stable and comfortable prosthesis.

DRAWINGS

These and other features, aspects, and advantages of the present invention will become better understood with reference to the following description, appended claims, and accompanying drawings where:

DESCRIPTION

With reference to the Figures, an apparatus 10 for modeling the pelvic anatomy 12 of a patient 14, also referred to herein as a person, comprises a sizing assembly 16 that does the actual modeling. The apparatus also includes adjustment means for adjusting the vertical position of a sizing assembly 16 to accommodate patients of different leg length. For this purpose there is provided an upstanding member 18 that is generally vertically oriented on which the sizing assembly 16 is supported. The upstanding member is maintained in its upright position by a base 19 comprised of four legs 20, each having a rubber foot 22 at a ground engaging end 23, and attached at the opposed end 24 to a collar 26 that is slidable up and down a bottom portion 28 of the upstanding member 18. Each leg 20 is held in an appropriately sized hole 30 in the collar 26. The supporting base 19 also includes an interlink 32 for each leg 20 that pivotably connects the respective leg 20 to the bottom portion 28 of the upstanding member 18 below the collar 26. When the upstanding member 18 is supported on the floor, the bottom 34 of the upstanding member 18 and the four rubber feet 22 are on the floor. For each ease in setup and transportation, the collar 26 can be raised in the direction of the arrow 36 shown in FIG. 2 to collapse the legs 20 against the upstanding member 18. This construction is based upon that used for a heavy duty tripod for a camera.

Other support systems for the upstanding member 18 can be used. For example, the upstanding member 18 can be permanently mounted to a table of other piece of furniture, or be mounted on the ground in brackets, or inserted into hole in the floor. The particular support means for the upstanding member shows in the Figures has the advantages that it provides a strong and stable base for the upstanding member 18 and also is collapsible, allowing the apparatus to be easily transportable, such as in a golf club transport container.

In the version of the invention shown in the Figures, the upstanding member 18 is tubular, i.e., hollow inside, and has a horizontal cross-section that is generally annular in shape, i.e., the outside and inside peripheries are generally circular. However, the upstanding member can be solid, and can be any shape in cross-section, including rectangular, oval, and square.

The sizing assembly 16 comprises, as its main components, a sliding block 38, a mounting block 40, a pubis stop arm 42 having a pubis stop 44 at its distal end (the end distal from the upstanding member 18), and a pelvic seat arm 46 supporting a pair of opposed ischial seats 48. The sliding block 38 has a front face 50 and a vertically oriented opening 52 therethrough that is sized and shaped so the sliding block 38 can move up and down along an upper portion 54 of the upstanding member 18.

A variety of different structures can be used as a means for adjusting the vertical position of the sizing assembly 16. In the version of the invention shown in FIG. 1, a rack and pinion system is used. A rack 56 is suspended downwardly from a bottom surface 58 of the sliding block 38. For this purpose, there is an opening (not shown) in the bottom surface 58 into which a top portion of the rack 56 fits, and is held in place by set screws (not shown). The rack 56 is mounted on the forward face 62 of the upstanding member 18. The pinion (not shown) is in a pinion collar 64 mounted on the upstanding member 18. The pinion collar 64 has a vertically oriented split 66 at the rear that can be opened with a tightening handle 68 at the end of a threaded pin 69 for moving the pinion collar 64 to a desired position on the upstanding member 18, and then tightened and clamped substantially closed for clamping the pinion collar 64 to a desired position. The rack 56, which is vertically movable along the upstanding member, slides in a vertically oriented slot 70 that extends through the pinion collar 64. By rotation of an adjustment handle 72 on the exterior of the pinion collar 64, the pinion is rotated, thereby causing the rack 56, and thus the size assembly 16, to move up and down along the upstanding member 18 for adjusting the vertical position of the sizing assembly 16 to accommodate persons of different leg length. Other adjustment means are within the scope of the present invention. For example, the upstanding member 18 can be made of multiple, such as two or more, telescoping sections with the sizing assembly secured to the upper telescoping section.

The sliding block 38 also has a vertically oriented slot 74 for opening and closing by means of a clamping handle 78 at the end of a threaded tightening pin 79 for clamping the sizing assembly 16 securely in place once it is at the desired vertical position on the upstanding member 18. In a simpler version of the present invention, the rack and pinion system can be eliminated, and the adjustment means can be any mechanism for securing the sizing assembly at a desired position along the upstanding member 18, such as the clamping system by itself, a pin slidable into a hole through the sliding block for engaging one of a series of spaced apart holes along the length of the upstanding member 18, by having the sliding assembly 16 held in place by a clamp mechanism, or as mentioned above, by having the sizing assembly securely fixed to the elongated member and having the elongated member adjustable in length such as by have the elongated member made of multiple telescoping sections.

Figure 7:
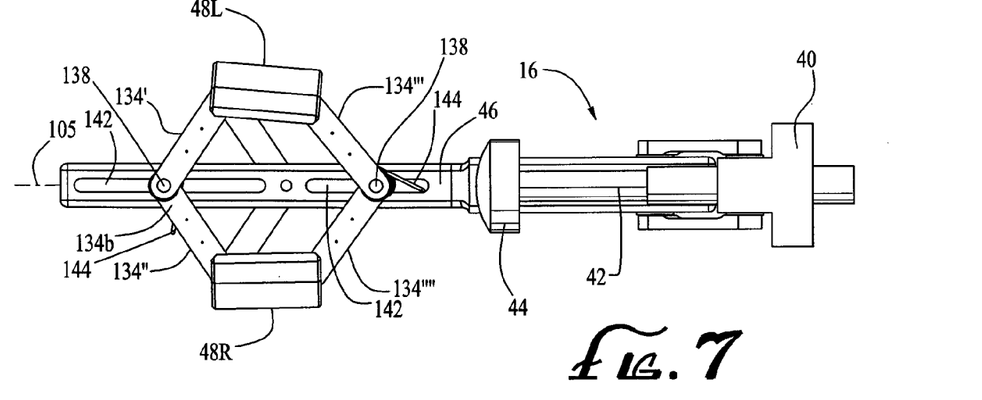
FIG. 7 is a top plan view of a portion of the pelvic arm sizing assembly shown in FIG. 1.
Figure 8:
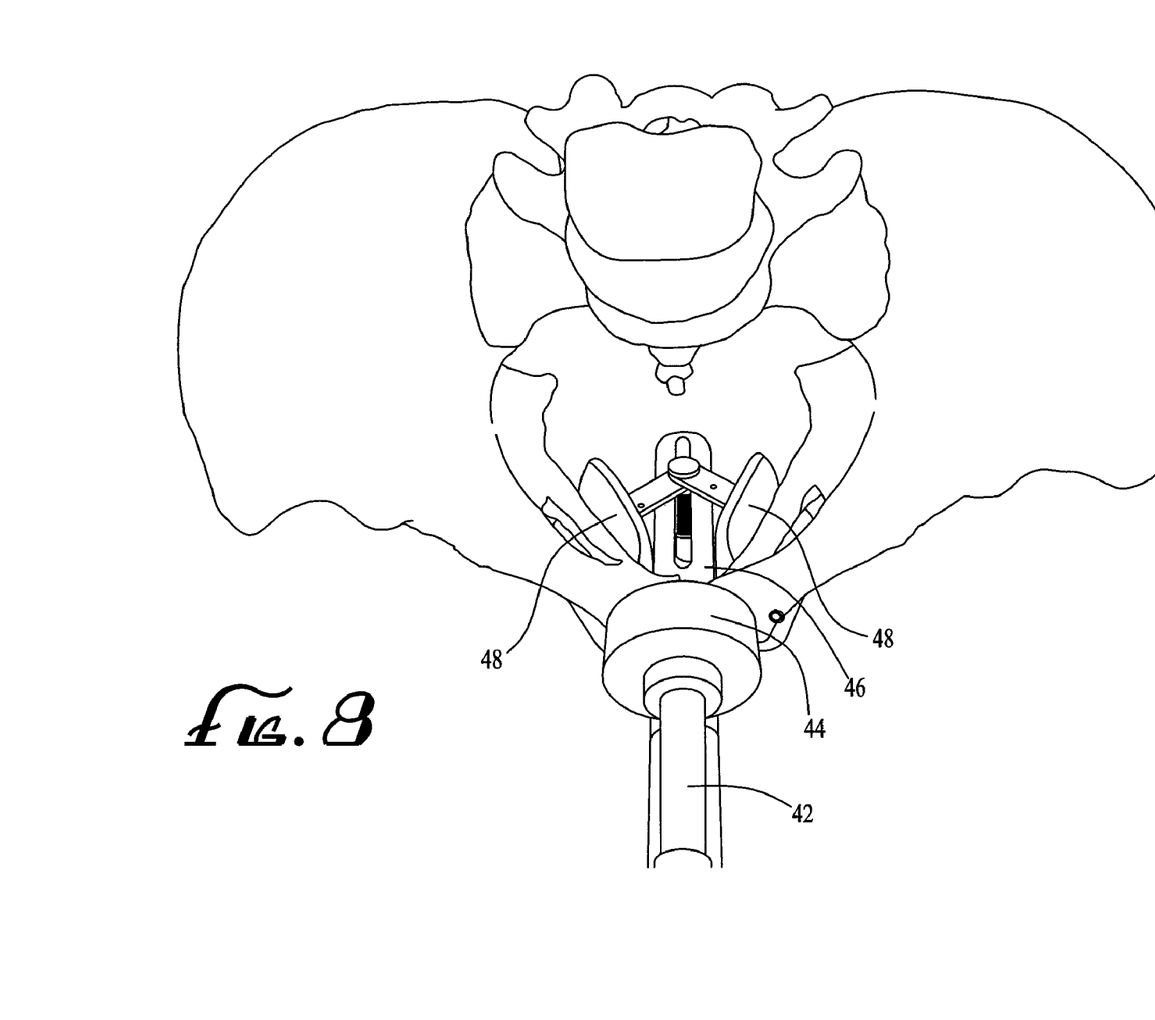
FIG. 8 shows the pelvic seat portion of the apparatus of FIG. 1 with regard to the pelvis of the patient; and vertical walls of the ischial seats with the pubis stop
Figure 9:
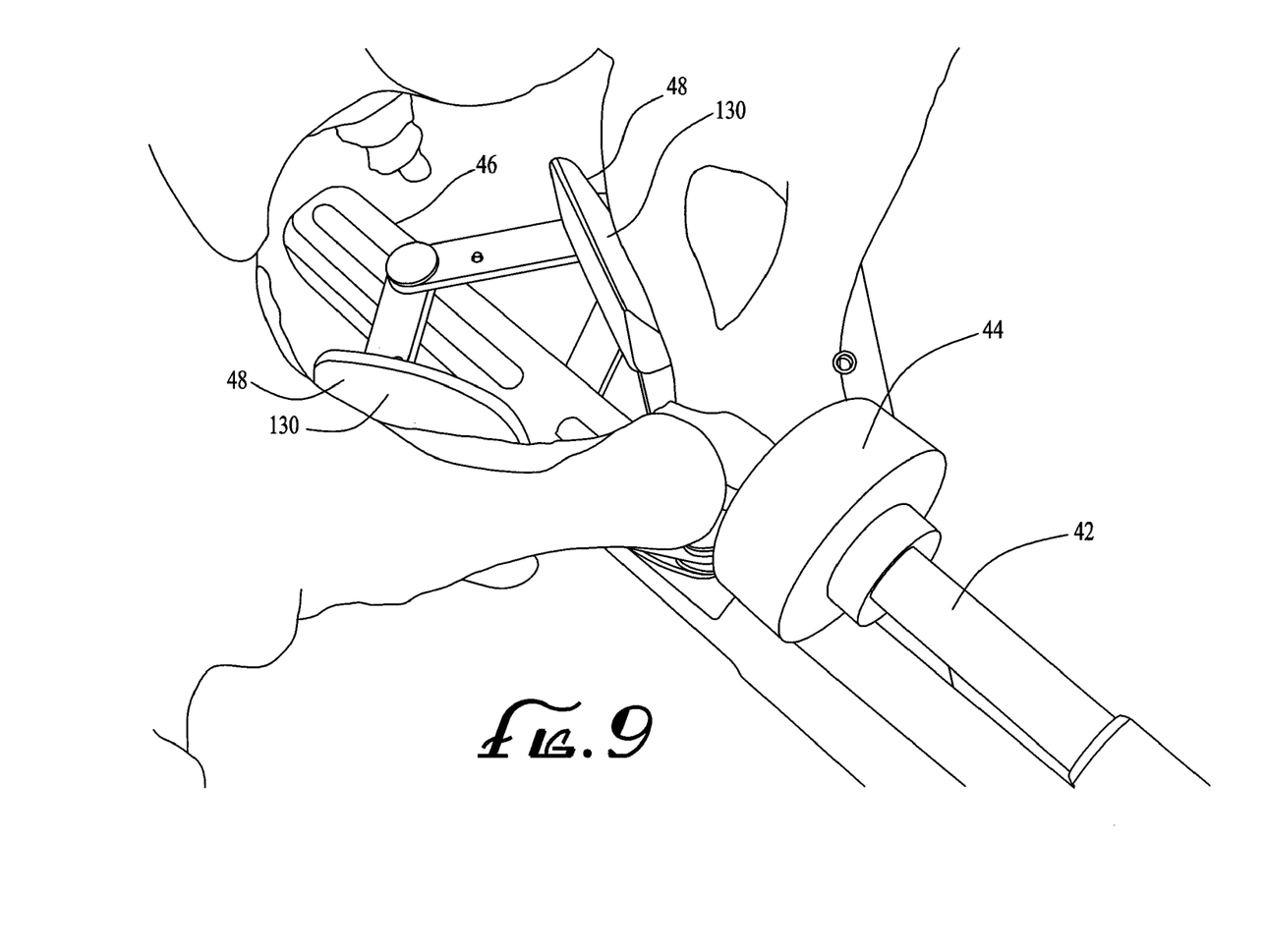
FIGS. 9-11 show portions of the sizing assembly of the apparatus of FIG. 1 engaging bones of a pelvis.
Figure 10:
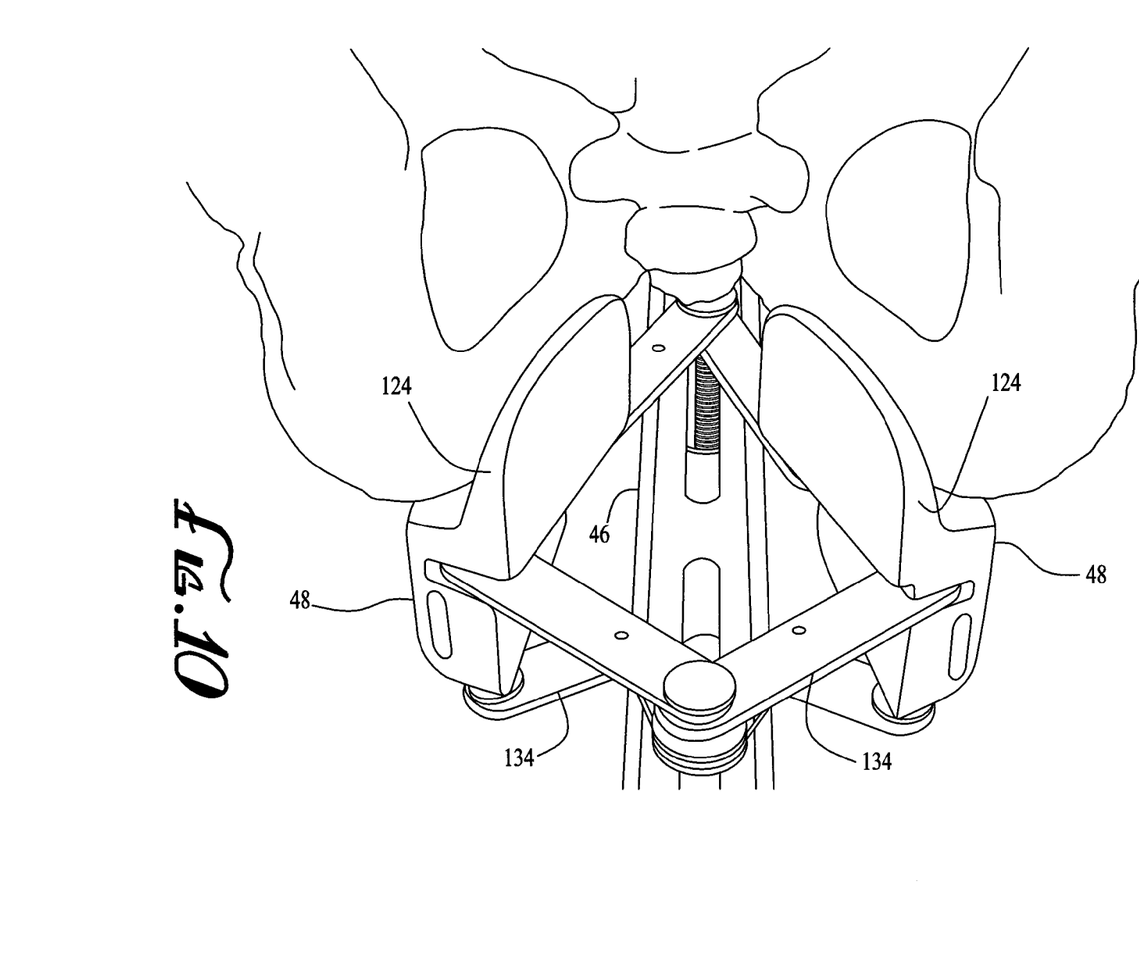
Figure 11:
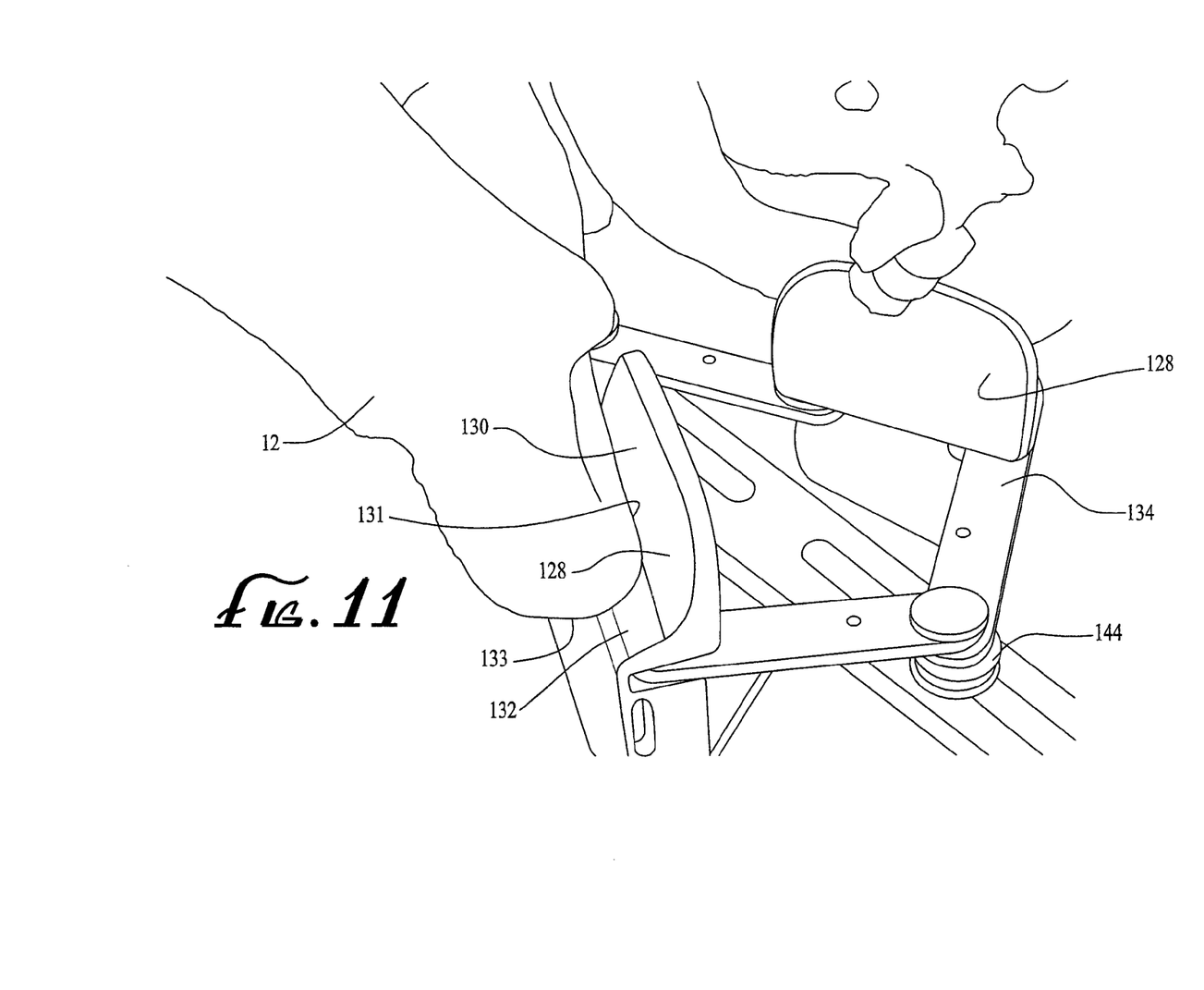

The mounting block 40 is secured to a front face 80 of the sliding block 38 by means of fasteners 82. The mounting block 40 is T-shaped in horizontal cross-section, as best shown in FIG. 7, having the top of the "T" against the front face 80 of the sliding block 38, and extending above a top surface 84 of the sliding block 38, thereby providing an extension 86 for supporting the pubis stop arm 42. The pubis stop arm 42 extends through a horizontally extending opening 88 in the extension 86, and is held securely therein by a set screw 90. The pubis stop arm 42 preferably comprises two telescoping sections, with an outer section 92 fixed in place in the extension 86 and an inner telescoping section 94 capable of telescoping within the outer section, and being locked in place by a rotating cam lock (not shown). The pubis stop arm is oriented generally horizontally, and thus is at an angle of about 90° relative to the vertical axis 91 of the upstanding member 18, and extends from the axis 91 of the upstanding member by a distance that can be varied. Thus the telescoping sections provide means for adjusting the distance between the pubis stop 44 and the ischial seats 48. Other versions of the pubis stop arm 42 are possible. For example, a pubis stop arm can be just a single horizontally extending tubular member slidable in the mounting block 40, whose position can be variably locked in place by means of a set screw or other type of fastener.

The pubis stop 44 is disc shaped having a smooth forward surface 96 for patient comfort.

Figure 1:
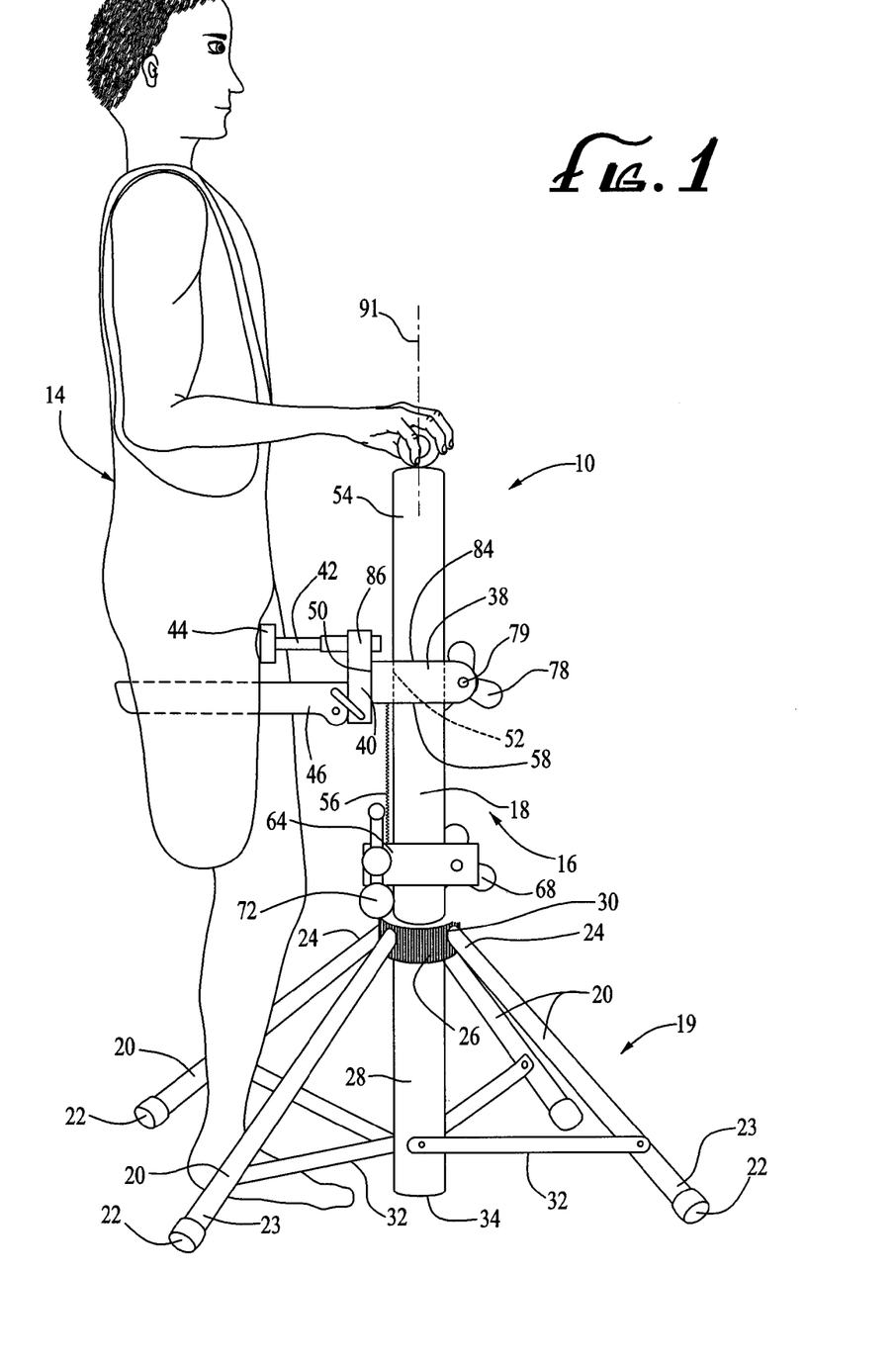
FIG. 1 is a side elevation view of an apparatus according to the present invention with a patient thereon.

The pelvic seat arm 46 is pivotally mounted to the mounting block 40 on a body portion 98 of the mounting block 40. This is accomplished with a pair of support arms 100. A first end section 100a of each arm 100 is mounted to a laterally facing surface 104 of the mounting block 40 with the opposed second end portion 100b secured to the pelvic seat arm 46. Each arm 100 is secured to the pelvic seat arm so that the pelvic seat arm can pivot between a horizontally extending position shown in FIG. 1 and a downwardly extending position (not shown) in which the longitudinal axis 105 of the pelvic seat arm 46 is substantially parallel to the longitudinal axis 91 of the upstanding member 18. This allows the pelvic seat arm to be moved out of the way during use of the apparatus 10 as described below. The pelvic seat arm 46 is securely latched in its up position, as shown in FIG. 1, by abutting against the upstanding member 18.

Figure 4:
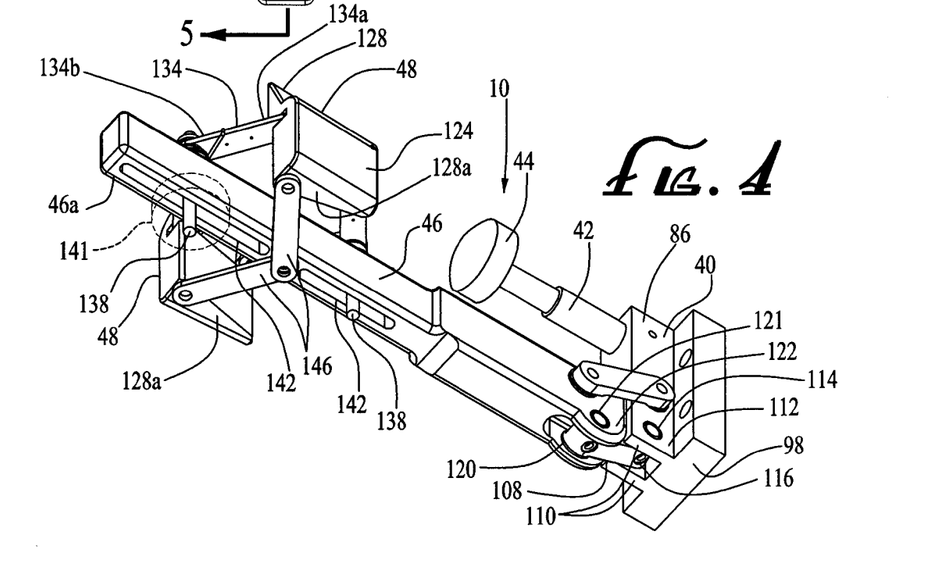
FIG. 4 is a perspective view of the pelvic arm sizing assembly of the apparatus of FIG. 1.
Figure 5:
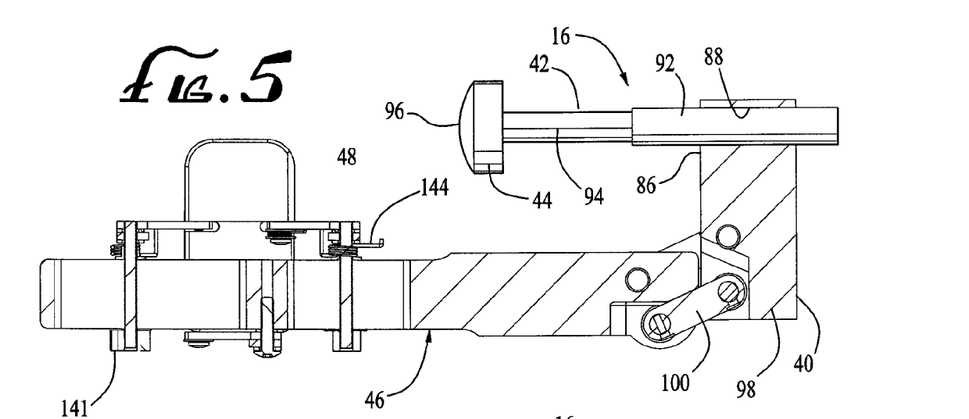
FIG. 5 shows a partial sectional view of the pelvic arm sizing assembly of FIG. 3 taken on line 5-5 in FIG. 3.
Figure 6:
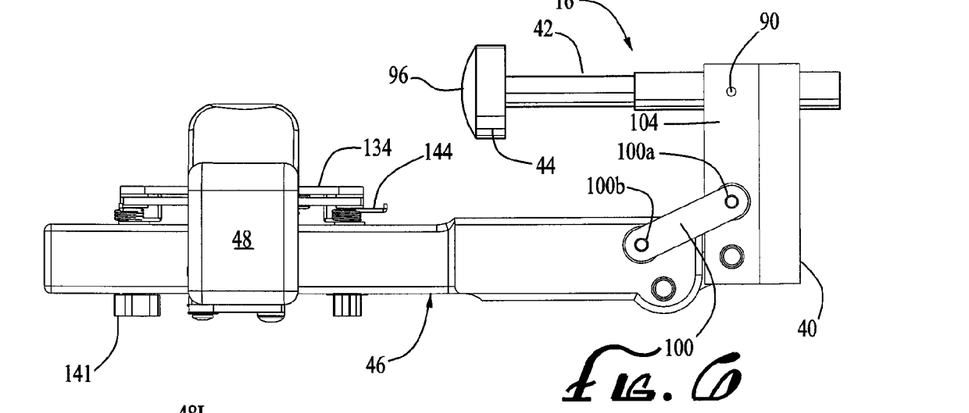
FIG. 6 is a side elevation view of the pelvic arm sizing assembly shown in FIG. 3.

The pelvic seat arm 42 is also securely mounted to the mounting block 40 by a mounting bracket 108 as shown in FIG. 4. The mounting bracket 108 is secured between a pair of opposed depending ears 110 on a bottom portion 112 of the mounting block 40 by means of a fastener 114 that extends horizontally through the ears 110 and a rearward portion 116 of the mounting bracket 108 which is between the ears 110. A forward portion of the mounting bracket 108 comprises a cylindrical collar 120. A fastener 121 extends through rearward located ears 122 of the pelvic seat arm 46. The fastener 121 is sized so as not to impede the pivoting motion of the pelvic seat arm 46.

The ischial seats 48 will now be described with regard to the orientation shown in FIG. 2 where the pelvic seat arm 46 is in its up position. Each ischial seat 48 is zig zag shaped, having an upstanding segment 124, a laterally extending segment 126 extending outwardly from the bottom of the upstanding segment 124, and a downwardly extending segment 128 depending from the outermost portion of the lateral segment 126. An outwardly facing face 130 of the upstanding segment 124 provides a substantially vertical wall for receiving a patient's medial aspect 131 of the ischial ramus, as shown in FIGS. 8-11. The upper surface 132 of the lateral segment 126 provides a horizontal ledge for receiving a patient's distal ischial tuberosity 133.

An important feature of the present invention is the adjustability of the sizing assembly 16 to accommodate the pelvic anatomy of different patients. For this purpose, the apparatus according to the present invention includes one or more of the following adjustments:

(1) the distance between the pubis stop 44 and the ischial seats 48;

(2) the distance between the ischial seats 48; and (3) the relative angle between the vertical wall, i.e., the outward face 130 of each ischial seat 46.

Figure 3:
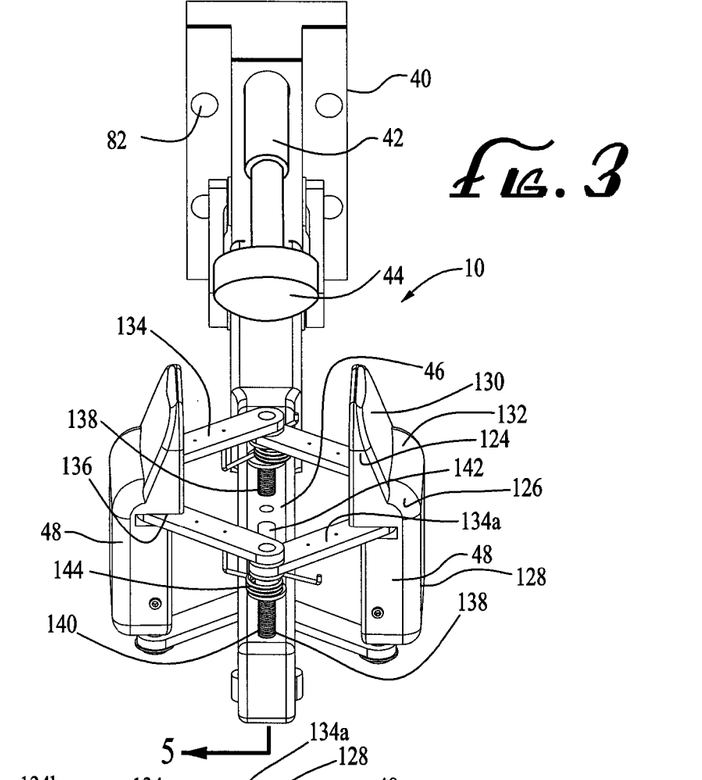
FIG. 3 is a top plan view of the pelvic arm sizing assembly of FIG. 1.

Thus, as best shown in FIGS. 3, 4, and 7, the ischial seats 48 are provided with a "scissor-type" adjustment assembly, comprising four ischial seat upper links 134, two for each ischial seat 48. One end 134a of each upper link 134 is pivotally secured to its respective ischial seat 48 on a bottom surface 136 of the lateral segment 126 of the seat 48, with the opposed end 134b pivotally mounted on a support rod 138 having a threaded end 140 with a tightening knob 141 for locking the ischial seats 48 in a desired position. Thus, as best shown in FIG. 7, one of the upper links 134' for the left seat 48L and one of the upper links 48" for the right seat 48R are on the same support rod 138, and the other upper link 134''' for the left seat 48L and another upper link 134'''' for the right seat 48R are on the other support rod 138. The directions "left" and "right" are from the perspective of the patient 14 as shown in FIG. 1.

The pelvic seat arm 46 has a pair of elongated slots 142 therein, one for each support rod 138, so the support rods can slide therein when not tightened. Each support rod 138 has a biasing spring 144 for biasing the ischial seats 48 apart.

The apparatus includes an additional pair of bottom link members 146, one for each seat. One end of each bottom link member 146 is pivotally secured to a downwardly facing surface 128a of the downwardly extending segment 128 with the other ends joined together on the bottom surface 46a of the pelvic seat arm 46.

The link system serves as means for adjusting the distance between the pelvic seats, and means for adjusting the relative angle between the vertical walls of the ischial seat.

Figure 2:
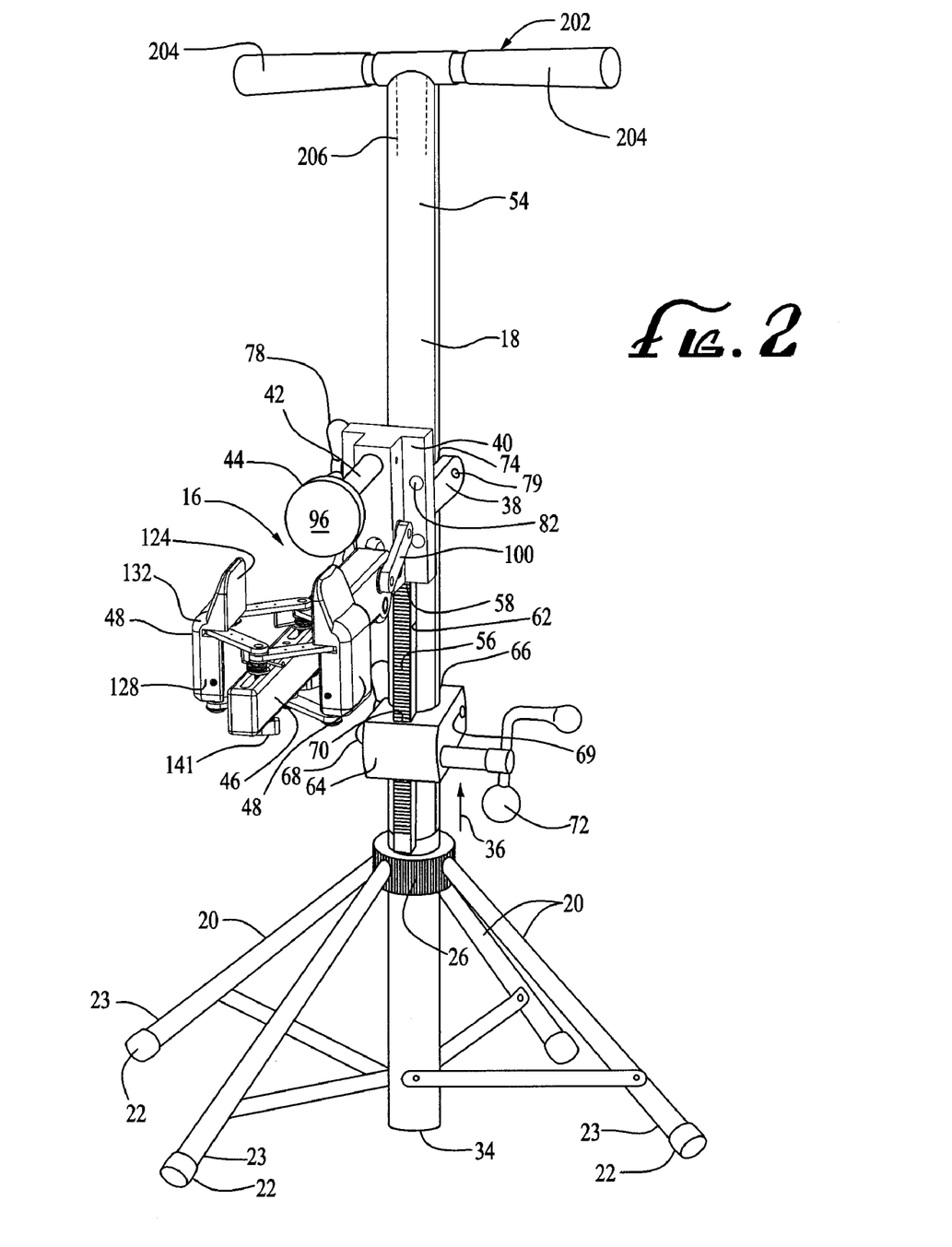
FIG. 2 is a front perspective view of the apparatus of FIG. 1.

An optional handle 202, best shown in FIG. 2, is provided for the patient 14, who is an transfemoral amputee, to support him or herself. The handle 202 is T-shaped, having a pair of laterally extending hand grips 204, and a downwardly extending tubular member 206 that removably slides into the top of the upstanding member 18. Optionally a permanently mounted handle can be provided, with the hand grips being pivotable downwardly for ease in transporting the apparatus 10.

The apparatus 10 can be made of any materials that provide suitable structural rigidity. Preferably, most of the components are made of metal such as steel or aluminum. Preferably the pubis stop 44 and the collar 26 are made of polymeric material, such as nylon.

In use of an apparatus according to the present invention, the following steps can be performed, but not necessarily in this exact order to fit a person for a transfemoral prosthesis:

1. The pelvic seat arm 46 is moved out of the way by pivoting it to its downward position.
2. The patient is positioned facing the apparatus 10 using the handle 202 for support.
3. The vertical position of the sizing assembly 16 is adjusted, and the lateral position of the pubis stop 44 is adjusted so that the pubis stop 44 is against the patient's pubis 203, as shown in FIGS. 8-11
4. The pelvic seat arm 46 is rotated upwardly and locked into position.
5. The tightening knobs 141 are loosened and the pelvic seats 48 are positioned until they come to rest on the medial aspect 131 of the ischial ramus complex of the patient.
6. The knobs 141 are then tightened.
7. The patient's ischial location is palpated to try to have the horizontal ledge 132 against the patient's ischial tuberosity 133 and having the vertical wall 130 up against the patient's medial aspect 131 of the ischial ramus.
8. The patient's pelvis is checked to make sure all parts of the apparatus are at the correct height and at the correct angles.
9. The pelvic seat arm 46 is rotated downwardly.
10. Optionally, there can be a cover on the pelvic seat. the cover can be made of plastic with a thickness about the same as the wrap thickness of a plaster bandage so that the casting that is made accommodates for the thickness of the plaster bandage. If the cover is used, it is removed at this time.
11. A protective plastic cover is placed over the entire pelvic arm and pubic stop.
12. A stockinette is placed over the patient's residual limb, as well as the patient's perineum.
13. A plaster bandage is wrapped on the residual limb.
14. The pelvic seat arm is raised and locked in place.
15. The patient applies pressure to the pubis stop and the ischial seats to ensure a proper impression on the plaster bandage is obtained.
16. While the plaster bandage cures, pressure is applied to the patient's soft tissue to ensure correct angles and proper definition on the residual limb. Effectively, the patient sits on the ischial seat, while pressing forwardly against the pubis stop. Thus a pair of mechanical seats having a fixed spatial orientation relative to each other are used to form a cast. This compares favorably against the cement process where it is necessary to try to manually press against the plaster bandage for about 20 minutes, a very tiring and difficult task.

This produces a "negative" cast which is used for forming the prosthetic socket.

The apparatus and method of the present invention have significant advantages. In particular, they accommodate the anatomy of different patients. The apparatus insures definition in the casting process that is not possible by the human hand. In addition, the apparatus is easy to use, and easy to assemble and disassemble.

Although the present invention is described in considerable detail with regard to certain preferred versions thereof, other versions are possible. For example, not all of the steps identified for use of the apparatus 10 need be performed for every patient. Therefore, the spirit and scope of the present invention should not be limited to the description of the preferred versions contained therein.

What is claimed is:

1. Apparatus suitable for modeling the pelvic anatomy of a person comprising:
   (a) a sizing assembly comprising;
      (i) a pubis stop arm having a pubis stop thereon; and
      (ii) a pelvic seat arm supporting a pair of opposed ischial seats, the pelvic seat arm extending generally horizontally from the upstanding member and being below the pubis stop, each ischial seat having a horizontal ledge for receiving a person's ischial tuberosity and an adjoining vertical wall for receiving a person's medial aspect of the ischial ramus, wherein the distance between the pubis stop and the ischial seats is adjustable, the distance between the ischial seats is adjustable, and the relative angle between the vertical walls of the ischial seats is adjustable to accommodate different anatomies; and
   (b) adjustment means for adjusting the vertical position of the sizing assembly to accommodate persons of different leg length.

2. The apparatus of claim 1 wherein the adjustment means comprises an upstanding member that supports the sizing assembly.

3. The apparatus of claim 1 wherein the adjustments means comprises means for moving the sizing assembly up and down along at least a portion of the upstanding member.

4. Apparatus for modeling the pelvic anatomy of a person comprising:
   (a) a support comprising a base and an upstanding member;
   (b) a sizing assembly supported by the upstanding member and movable vertically to selected positions thereon to accommodate persons of different leg length, the sizing assembly comprising;
      (i) a pubis stop arm having a pubis stop thereon; and
      (ii) a pelvic seat arm supporting a pair of opposed ischial seats, the pelvic seat arm extending generally horizontally from the upstanding member and being below the pubis stop, each ischial seat having a horizontal ledge for receiving a person's ischial tuberosity and an adjoining vertical wall for receiving a person's medial aspect of the ischial ramus, wherein the distance between the pubis stop and the ischial seats is adjustable, the distance between the ischial seats is adjustable, and the relative angle between the vertical walls of the ischial seats is adjustable to accommodate different anatomies.

5. The apparatus of claim 1 wherein the pelvic seat arm can pivot downwardly.

6. The apparatus of claim 1 comprising at least one handle so a person missing a portion of a leg can support themselves.

7. The apparatus of claim 4 comprising at least one handle so a person missing a portion of a leg can support themselves.

8. The apparatus of claim 6 wherein the handle is supported by the upstanding member.

9. The apparatus of claim 2 wherein the pubis stop arm extends generally horizontally from the upstanding member.

10. The apparatus of claim 1 wherein the pubis stop arm length is adjustable.

11. The apparatus of claim 10 wherein the pubis stop arm comprises telescoping members for adjustment of the length of the pubis stop arm.

12. The apparatus of claim 2 wherein the pelvic seat arm is supported by the upstanding member below the position where the pubis stop arm is supported by the upstanding member.

13. The apparatus of claim 1 comprising means for adjusting the length of the pubis stop arm.

14. The apparatus of claim 1 comprising means for adjusting the distance between the ischial seats.

15. The apparatus of claim 1 comprising means for adjusting the relative angle between the vertical walls of the ischial seats.

16. The apparatus of claim 4 comprising means for adjusting the relative angle between the vertical walls of the ischial seats.

17. The apparatus of claim 1 wherein the pelvic seat arm comprises scissor members for adjusting the distance between the ischial seats and the relative angle between the vertical walls of the ischial seats.

18. The apparatus of claim 4 wherein the sizing assembly is movable up and down at least a portion of the upstanding member.

19. The apparatus of claim 4 comprising means for moving the sizing assembly up and down at least a portion of the upstanding member.

20. A method for fitting a person for a transfemoral prosthesis comprising the steps of:
   (a) selecting the apparatus of claim 4;
   (b) adjusting the position of the sizing assembly and the length of the pubis stop arm to position the pubis stop against the person's pubis; and
   (c) positioning the pelvic seat against the person's ischium tuberosity and medial aspect of the ischium ramus.

21. A method for fitting a person for a transfemoral prosthesis comprising the steps of:
   (a) selecting the apparatus of claim 10;
   (b) adjusting the position of the sizing assembly and the length of the pubis stop arm to position the pubis stop against the person's pubis; and
   (c) positioning the pelvic seat against the person's ischium tuberosity and medial aspect of the ischium ramus.

22. The method of claim 21 wherein the pelvic seat arm can pivot downwardly between a down position and an up position, and further comprising having the pelvic seat arm in the down position before step b, and pivoting the pelvic seat arm to its up position after step b and before step c.

23. The method of claim 21 comprising the additional step of applying a plaster bandage to the person after step c.

24. The method of claim 16 comprising the additional step, before step (c), of placing a cover on the ischial seat to accommodate for the thickness of the plaster bandage and removing the cover after step c and before applying the plaster bandage.

* * * * *